United States Patent
McKay (10) Patent No.: US 8,968,323 B2
(45) Date of Patent: Mar. 3, 2015

(54) BONE GRAFT INJECTION SYRINGE

(75) Inventor: William F. McKay, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 524 days.

(21) Appl. No.: 12/951,655

(22) Filed: Nov. 22, 2010

(65) Prior Publication Data

US 2012/0130386 A1  May 24, 2012

(51) Int. Cl.
*A61B 17/58* (2006.01)
*A61B 17/88* (2006.01)

(52) U.S. Cl.
CPC .................................. *A61B 17/8825* (2013.01)
USPC .......................................................... 606/94

(58) Field of Classification Search
USPC .............. 606/92, 93, 94; 604/15, 57, 94, 187, 604/218
See application file for complete search history.

(56) References Cited

U.S. PATENT DOCUMENTS

| | | | |
|---|---|---|---|
| 4,239,113 A * | 12/1980 | Gross et al. ................... | 206/568 |
| 5,073,114 A | 12/1991 | Detsch | |
| 5,951,160 A | 9/1999 | Ronk | |
| 6,098,666 A * | 8/2000 | Wells et al. ................... | 138/115 |
| 6,325,804 B1 | 12/2001 | Wenstrom, Jr. et al. | |
| 6,676,664 B1 * | 1/2004 | Al-Assir ......................... | 606/94 |
| 6,723,131 B2 | 4/2004 | Muschler | |
| 7,018,089 B2 | 3/2006 | Wenz et al. | |
| 7,018,382 B2 | 3/2006 | Merboth et al. | |
| 7,513,901 B2 | 4/2009 | Scifert et al. | |
| 7,615,030 B2 | 11/2009 | Murphy et al. | |
| 7,671,014 B2 | 3/2010 | Beals et al. | |
| 7,740,632 B2 | 6/2010 | Young | |
| 2002/0045942 A1 | 4/2002 | Ham | |
| 2002/0112981 A1 | 8/2002 | Cooper et al. | |
| 2003/0069545 A1 | 4/2003 | Arm | |
| 2003/0236573 A1 | 12/2003 | Evans et al. | |
| 2004/0068234 A1 | 4/2004 | Martin et al. | |
| 2004/0068264 A1 | 4/2004 | Treace | |
| 2004/0071668 A1 | 4/2004 | Bays et al. | |
| 2004/0167617 A1 | 8/2004 | Voellmicke et al. | |
| 2005/0070915 A1 * | 3/2005 | Mazzuca et al. ................ | 606/93 |
| 2005/0234493 A1 * | 10/2005 | Carr et al. ...................... | 606/181 |
| 2007/0026030 A1 | 2/2007 | Gill et al. | |
| 2007/0233146 A1 | 10/2007 | Henniges et al. | |
| 2008/0152691 A1 | 6/2008 | Drapeau et al. | |
| 2008/0214998 A1 | 9/2008 | Kurek et al. | |
| 2009/0142385 A1 | 6/2009 | Gross et al. | |
| 2009/0204120 A1 * | 8/2009 | Trosken et al. ................. | 606/93 |
| 2009/0254104 A1 | 10/2009 | Murray | |
| 2009/0275947 A1 * | 11/2009 | Graham et al. ................. | 606/71 |
| 2009/0306671 A1 | 12/2009 | McCormack et al. | |
| 2010/0056989 A1 * | 3/2010 | McKay ........................... | 604/28 |

* cited by examiner

*Primary Examiner* — Christian Sevilla
(74) *Attorney, Agent, or Firm* — Sorell Lenna & Schmidt LLP (57) ABSTRACT

A syringe that has a barrel with curvature is provided. The curvature enables a greater volume of bone graft materials to be housed than in a straight syringe without increasing the absolute distance from the handle of the plunger to dispensing end of the syringe. Additionally by maintaining a constant diameter, the barrel permits bone graft material to be dispersed with reduced likelihood of clogging.

19 Claims, 8 Drawing Sheets

BONE GRAFT INJECTION SYRINGE

BACKGROUND

Voids in bones may exist because a diseased portion of the bone has been surgically removed or a bone has been damaged in an accident. These voids can lead to discomfort and structural instability, either of which may prompt a patient to seek ways to alleviate the pain and to obtain more structural support.

In response to these conditions associated with the presence of bone voids, researchers and clinicians have developed many different materials to fill the voids or to cause fusion between adjacent bones or between segments of a bone. These materials include, but are not limited to, temporary or permanent bone substitute materials that may be accompanied by one or more agents that help to promote healing.

However, the challenge of filling a bone void rests not only in formulating a suitable composition, but also in delivering the composition to the site of interest. One type of tool that is useful for the delivery of certain known compositions is the plunger type syringe.

Unfortunately, known syringes are imperfect because too frequently, material within the barrels of those syringes clog when bone graft material is the substance that one seeks to dispense. This causes either too much fluid or only fluid to be expelled from the syringe. Consequently, dehydrated bone graft material may become stuck inside the syringe barrel. Therefore, there is a need for new syringe designs that can more efficiently administer bone graft materials that are prone to clogging.

SUMMARY

Devices and methods for injecting bone graft materials into bone defects or bone grafting sites are provided. Through the use of these devices and methods, bone graft materials that are prone to clogging during delivery may be more efficiently delivered to a site of interest.

According to an embodiment of the present invention, there is a syringe assembly for dispensing bone graft material comprising a barrel having a first opening and a second opening, the barrel defining a cavity with curvature; and a flexible plunger, wherein the flexible plunger is sized to slide within and at least part of the plunger into and out of the cavity. Optionally, the syringe assembly will also comprise a cover for the first opening, wherein the cover optionally comprises a reversibly sealable opening such as a valve that allows substances to enter and to exit the cavity.

According to another embodiment of the present invention, there is a method for injecting bone graft materials comprising: loading a syringe comprising a barrel having a first opening and second opening, the barrel defining a curvature over at least ninety degrees; and a flexible plunger, wherein the flexible plunger is sized to slide within the cavity; and pushing the plunger toward the first opening, thereby forcing materials within the barrel to exit the syringe.

In various embodiments, the devices and methods of the present invention make use of a barrel that has a constant internal diameter. By creating a barrel that curves, the amount of material that is contained within the syringe can be increased without increasing the distance between the plunger and the needle. Furthermore, if the cross-section of the barrel is kept constant, compaction and clogging of the barrel by particulate material in the grafting material can be minimized. Additionally, in order to avoid clogging at the end at which material is dispensed, in some embodiments it may be advantageous for the opening at that end to have the same cross-section as the barrel or a cross-section that is larger than that of the barrel.

BRIEF DESCRIPTION OF THE FIGURES

In part, other aspects, features, benefits and advantages of the embodiments of the present invention will be apparent with regard to the following description, appended claims and accompanying drawings where:

It is to be understood that the figures are not necessarily drawn to scale. Further, the relation between objects in the figures may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and the appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters set forth herein are in some instances approximations, the numerical values set forth in the specific examples or embodiments are reported as precisely as possible. Any numerical value, however, inherently contains certain errors necessarily resulting from the standard deviation found in the respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that the invention is not intended to be limited to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Definitions

It is noted that, as used in this specification and the appended claims, the singular forms "a," "an," and "the," include plural referents unless expressly and unequivocally limited to one referent.

As used herein, "bone graft material" refers to, for example, autogenous morselized bone graft, autogenous bone graft strips, allograft chips, demineralized bone matrix in putty, gel, or other forms, xenografts and fired bone, bone graft substitutes, such as hydroxyapatite, calcium carbonate, beta tricalcium phosphate, calcium sulfate or mineralized collagen, collagen-ceramic mixtures, natural or synthetic polymers, such as collagen particles, meshes, sponges, and gels, hyaluronic acid and derivatives thereof, liposomes or other natural biomaterials known as potential implants, or carriers of therapeutic agents, such as cytokines, growth factors, cells, antibiotics, analgesics, chemotherapeutic drugs, and the like, synthetic polymers, such as alpha-hydroxy polyesters, including polylactic acid, polyglycolic acid and their copolymers, polydioxanone, as well as poly methyl methacrylate, separately, in mixture or in admixture with any therapeutic agents, and bone graft replacements, such as recombinant bone morphogenetic proteins. In at least one embodiment, bone graft material includes granules sold under the tradename MasterGraft™.

The term "practitioner" or "user" means a person who uses or is using the methods and/or devices of the current disclosure on the patient. These terms include, without limitation, doctors (e.g., surgeons, interventional specialists, and physicians), nurses, nurse practitioners, other medical personnel, clinicians, veterinarians, and scientists.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

The term "syringe" refers to a device that has a barrel and plunger. Material may be placed in the barrel by drawing back upon the plunger, which is in the barrel. The negative pressure in the barrel draws the material through an opening e.g., the end of the barrel itself or through a hollow needle and up into the barrel. The needle (which includes all thin hollow tubes, regardless of how sharp they are), when present, may be attached to the barrel through an adapter such as a valve at the first opening. The adapter when present connects the needle to the barrel and may for example, comprise a valve that can seal the connection between the barrel and the needle and then upon exertion or removal of an appropriate force open the connection between the barrel and the needle. Alternatively there may be no needle and the material may enter and exit the barrel directly through a spout and/or adapter and/or valve and/or end of the barrel. In other embodiments, material may be placed into the barrel through an opening or port that can be closed (e.g., sealed) that is not the opening or port through which material is deposited at a site of interest. Thus, the material may be loaded through an opening in the barrel on for example the side of the barrel. Material can be dispensed by pushing down upon the plunger.

As noted above, associated with the syringe or as part of the syringe assembly there may also be a needle. In some embodiments, the needle may be used to hydrate bone graft material prior to injecting it, but the bone graft material is no loaded through the needle.

The term "treating" and the phrases "treatment of a disease" and "treatment of a condition" refer to executing a protocol that may include the use of the devices and methods herein and/or administering one or more bone graft materials to a patient (human, normal or otherwise, or other mammal), in an effort to diagnose and/or to alleviate signs or symptoms of the disease or condition. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes, but includes protocols that have only a marginal effect on the patient.

Syringes

In one embodiment, there is a bone graft injection syringe assembly for dispensing bone graft material. The syringe comprises a barrel and a flexible plunger.

The barrel has a first opening and optionally a second opening. The barrel defines a cavity with a curvature over at least ninety degrees. A "cavity with a curvature" is in its simplest embodiment, a cavity that has a center that moves along an arc. The arc may for example have a constant radius, or it may have increasing and/or decreasing radius. For example, the arc may have a constant radius over about 90 degrees to about 360 degrees or over about 90 degrees to about 120 degrees or over about 120 degrees to about 150 degrees or over about 150 degrees to about 180 degrees or over about 180 degrees to about 210 degrees or over about 210 degrees to about 240 degrees or over about 240 degrees to about 270 degrees or over about 270 degrees to about 320 degrees or over about 320 degrees to about 360 degrees.

If the radius increases or decreases, then the barrel may be referred to as forming a spiraling arc. The phrase spiraling arc includes arcs that extend over more than 360 degrees and arcs that extend over less than 360 degrees. The spiraling arc may in some embodiments have an increasing or decreasing radius over about 90 degrees to about 720 degrees or over about 90 degrees to about 120 degrees or over about 120 degrees to about 150 degrees or over about 150 degrees to about 180 degrees or over about 180 degrees to about 210 degrees or over about 210 degrees to about 240 degrees or over about 240 degrees to about 270 degrees or over about 270 degrees to about 320 degrees or over about 320 degrees to about 360 degrees or over about 360 degrees to about 420 degrees or over about 420 degrees to about 480 degrees or over about 480 degrees to about 540 degrees or over about 540 degrees to about 600 degrees or over about 600 degrees to about 660 degrees or over about 660 degrees to about 720 degrees or more. Further, the rate of the increase in radius may be constant or irregular and a barrel may, in some embodiments have ranges that have portions with increasing radii and constant radii or portions with decreasing radii and constant radii or portions with both increasing and decreasing radii and optionally one or more portions with constant radii. In some embodiments, the radii move in two-dimensions and in some embodiments, they move in three-dimensions.

The cavity of the barrel may have an irregular or regular three dimensional shape such as a tube that possesses curves that move in either a clockwise or counterclockwise direction. In some embodiments, the barrel maintains a constant lumen size. Thus, the barrel may form a tube or cylinder with a constant diameter. In some embodiments, the cross-section of the tube or cylinder is a circle, an oval or an ellipse.

In some embodiments, the curvature forms a cylindrical coil. A cylindrical coil is a shape that when viewed from a side, appears to be similar to a coil. Thus, the barrel may, for example, form a coil that has a real or imaginary axis that is oriented parallel to one or both ends of the barrel and/or the plunger, and the coils loop around the axis. The end of the barrel through which the plunger is moved may be connected to (and in some embodiments, run seamlessly into) the coil either at an edge of the coil or away from the edge, e.g., in the center of coil through a pieces that forms a cavity that is connected to a portion of the barrel along the edges of the barrel. Similarly, the other end of the barrel (the dispensing end) may be connected to (and in some embodiments, run seamlessly into) the coil section either at an edge of the coil or away from the edge, e.g., in the center of coil through a pieces that forms a cavity that is connected to a portion of the barrel along the edge of the coil. The coils may have constant and/or variable (e.g., increasing or decreasing) radii.

The barrel may contain a first region that is not connected to the second region and the first region may terminate at a first opening through which substances can enter or exit the cavity. This first opening may be located at one end of the arc and optionally may comprise a short straight region of, for example, less than 5 cm, less than 4 cm, less than 3 cm, less than 2 cm, or less than 1 cm. This opening may for example comprise a valve that is reversibly closable, and thus protects the integrity of the contents of the barrel from being contaminated or dispensed undesirably. The valve may be in the form of an adapter that reversibly opens when subjected to positive and/or negative pressure may be located at the first opening. In some embodiments, materials may be dispensed through the adapter to the site of interest of through another piece that is connected to the adapter. Alternatively, there may be a cap that can be reversibly associated with this end to prevent leakage or contamination when the syringe contains bone graft material, but the syringe is not in use.

The second region may be straight, and may be where the plunger is loaded; however, in some embodiments, the barrel contains no regions that are straight. If there is a first region that is straight, this first region may be next to and seamlessly run into a region that contains the aforementioned arc curvature. The first region may in some embodiments run directly into an arc with a constant curvature (or constant radius) or the first region may run into the center of a hypothetical circle with the arc coming off of it and increasing its curvature or the first region may turn into the portion of the arc that has a decreasing radius of curvature at the arc's largest radius point. If the second region is straight, its length may, for example, be less than 5 cm, less than 4 cm, less than 3 cm, less than 2 cm, or less than 1 cm, and it may run directly into an arc with a constant curvature (or constant radius) or the second region may run into the center of a hypothetical circle with the arc coming off of it and increasing its curvature or the second region may turn into the portion of the arc that has a decreasing radius of curvature at the arc's largest radius point.

As noted above, the first end and the second end of the barrel may both have straight regions. These straight regions may have axes that are parallel to each other. They may alternatively not be parallel to each other. In some embodiments, they are parallel to each other but do not exist in the same plane. In some embodiments in which they are not parallel to each other, they are askew.

In some embodiments, the barrel has a valve that is situated somewhere along the length of the barrel. Through this valve, hydration prior to injection can be accomplished. There also may be one or more vents through which displaced air may escape.

The syringe assembly may also comprise a hollow needle, which may for example be attached to the front opening. The needle may be selected to be a size that has hollow tubing that is large enough for the bone graft material to move through, and long enough to provide access to the desired site. The needle may for example be attached to the syringe by a luer lock fitting, threading, friction fit connection or combinations thereof.

The syringe may also comprise a plunger that may in some embodiments be flexible, thereby allowing it to move through a curved barrel (e.g., by sliding). As persons of ordinary skill in the art are aware, a plunger has a first end that is in contact with the material to be pushed through the syringe. There is also a second end that is distal to the first end. Connecting the two ends is a rod, cylinder or other connecting structure (which may be referred to as a connector) that is designed in a manner that when a force is applied to the second end, the force transfers through the connector and to the first end, thereby pushing the material through the syringe. A flexible plunger is able to transfer this force while sliding within a curved barrel.

The plunger may be inserted into the second end of the barrel through the second opening of the barrel. In some embodiments, the plunger may be able to be completely disassociated from the barrel by a pulling force. In other embodiments, the connector may move through the second opening but the first end of the plunger, which may have a greater diameter than the connector is precluded from moving through the second opening by a physical structure at the end of the barrel.

In some embodiments the length of the barrel is from about 5 cm to about 50 cm or about 5 cm to about 10 cm or about 10 cm to about 20 cm or about 20 cm to about 30 cm or about 30 cm to about 40 cm or about 40 cm to about 50 cm. The length is measured with respect to the distance traveled along the path of the barrel.

In some embodiments, the cross-section of the barrel is a circle and has an internal radius of about 0.1 cm to about 1 cm or about 0.2 cm to about 0.4 cm or about 0.3 cm to about 0.6 cm or about 0.6 cm to about 1 cm.

In some embodiments, the volume of the barrel is from about 0.1 cc to about 50 cc or from about 1 cc to about 5 cc or from about 2 cc to about 10 cc or from about 4 cc to about 20 cc or from about 10 cc to about 20 cc or from about 20 cc to about 30 cc or from about 25 cc to about 40 cc or from about 30 cc to about 50 cc.

The plunger preferably has a connector that enables it to be pushed sufficiently far in the barrel to force out the material contained therein. The combined size of the length of the connector and the thickness of the end of the plunger that pushes the material is in some embodiments at least as long as the length of the barrel. The plunger may in some embodiments have a spacer attached to it that contacts the bone graft material and enhances expulsion of it when force is applied to the plunger, thereby causing it to slide and to expel the bone graft material.

The end of the barrel through which material is dispensed to a site of interest may in some embodiments have a cross-section that is the same as the cross-section of the barrel or at least 70%, or at least 80% or at least 90% of the cross-section of the lumen of the barrel. Note that when the barrel has lumen cross-sections that vary, the aforementioned percentages are relative to the widest cross-sections.

The barrel of the present invention may be made by methods that are now known to persons of ordinary skill in the art for manufacturing syringe tubes or that become known, and that upon reading this disclosure, become appreciated as being of use in connection with the present invention. In order to obtain a barrel with curvature, one may wind up a flexible plastic tube and place it in a cartridge or injection molding chamber design. One may then place a cap on top.

In some embodiments, the syringe is ergonomically designed. The ergonomic design may for example comprise finger adapters and/or an hourglass outer body. By way of a non-limiting example, there may be a pair of opposed finger grips at one end and a bayonet mount at the other end. The finger grips may, for example, include a D-shaped ring and a curved finger rest extending from the barrel to allow the practitioner to grip the syringe assembly while sliding the plunger through the barrel.

In various embodiments, the device includes dose indicator markings (e.g., numbers, lines, letters, radiographic markers, etc.) to indicate the amount of material delivered. For example, the barrel of the syringe may contain markings in cubic centimeters, millimeters or ounces or combinations thereof.

Figure 1A:
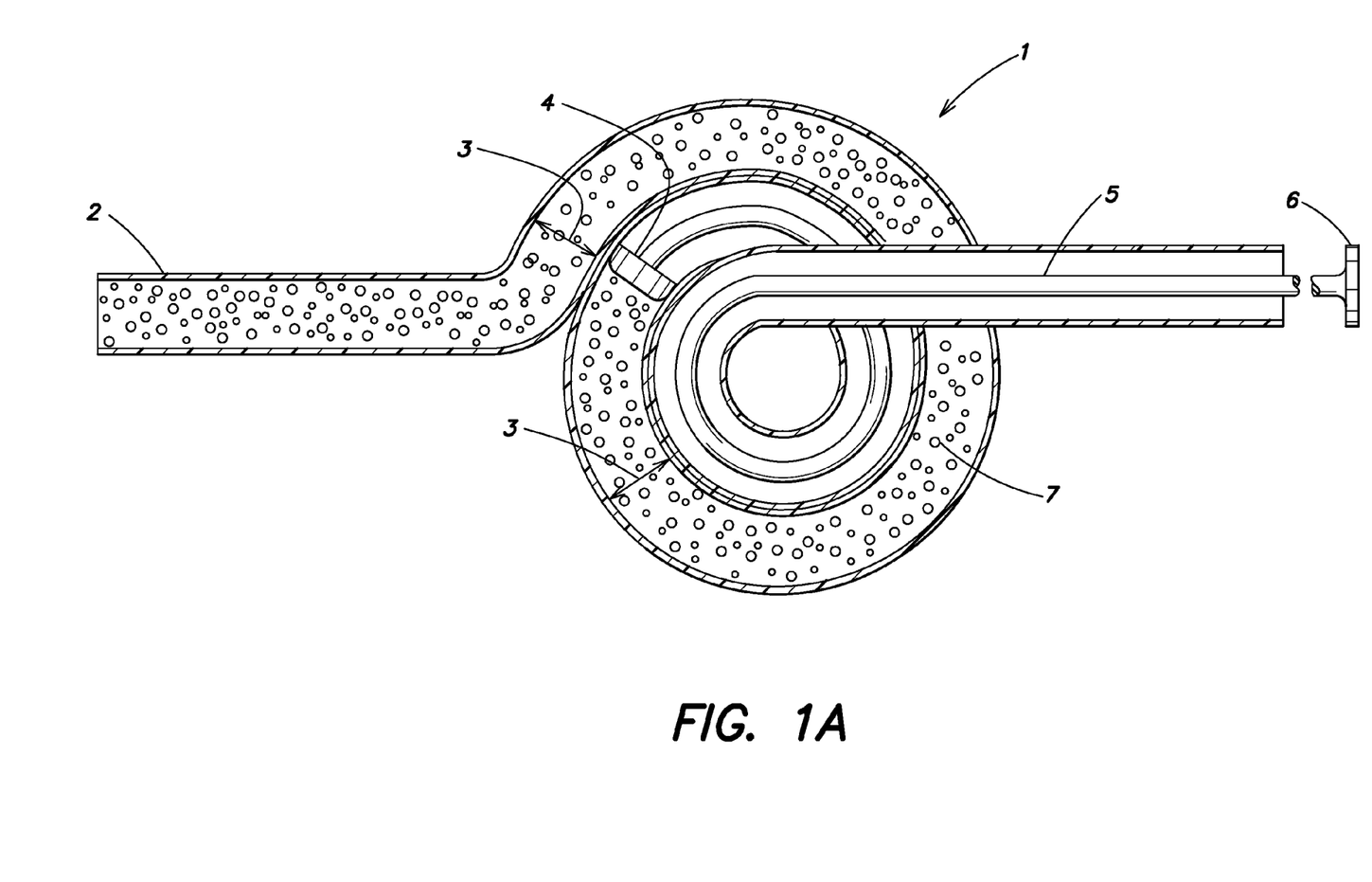
FIG. 1A is a representation of an embodiment of a bone graft injection syringe according to the present invention, with a blunt dispensing end.

Certain embodiments of the present invention may be further understood by reference to the accompanying figures. In FIG. 1A, a syringe 1 is shown. At a first end 2 bone graft material may be loaded and dispensed.

At the other end is a plunger 6 with a flexible connection part 5 (also known as a connector) that can bend along the arc of the barrel of the syringe. The connector is shown with a break to denote that its length is longer than shown in the figure. The end of the plunger (the spacer) 4 that contacts the bone graft material spans the lumen of the barrel 3, which is constant. The spacer may be designed of a material (e.g., rubber) and be a size that prevents backflow of bone graft material. Thus, it forms a movable seal. The syringe is shown containing bone graft material 7 that can be pre-loaded by a manufacturer or loaded by a practitioner at the time of use.

Note that the barrel is not limited to a 2-dimension plane. A first section is shown in the foreground, and the second section, which has an increasing curvature, runs behind the first section.

Figure 1B:
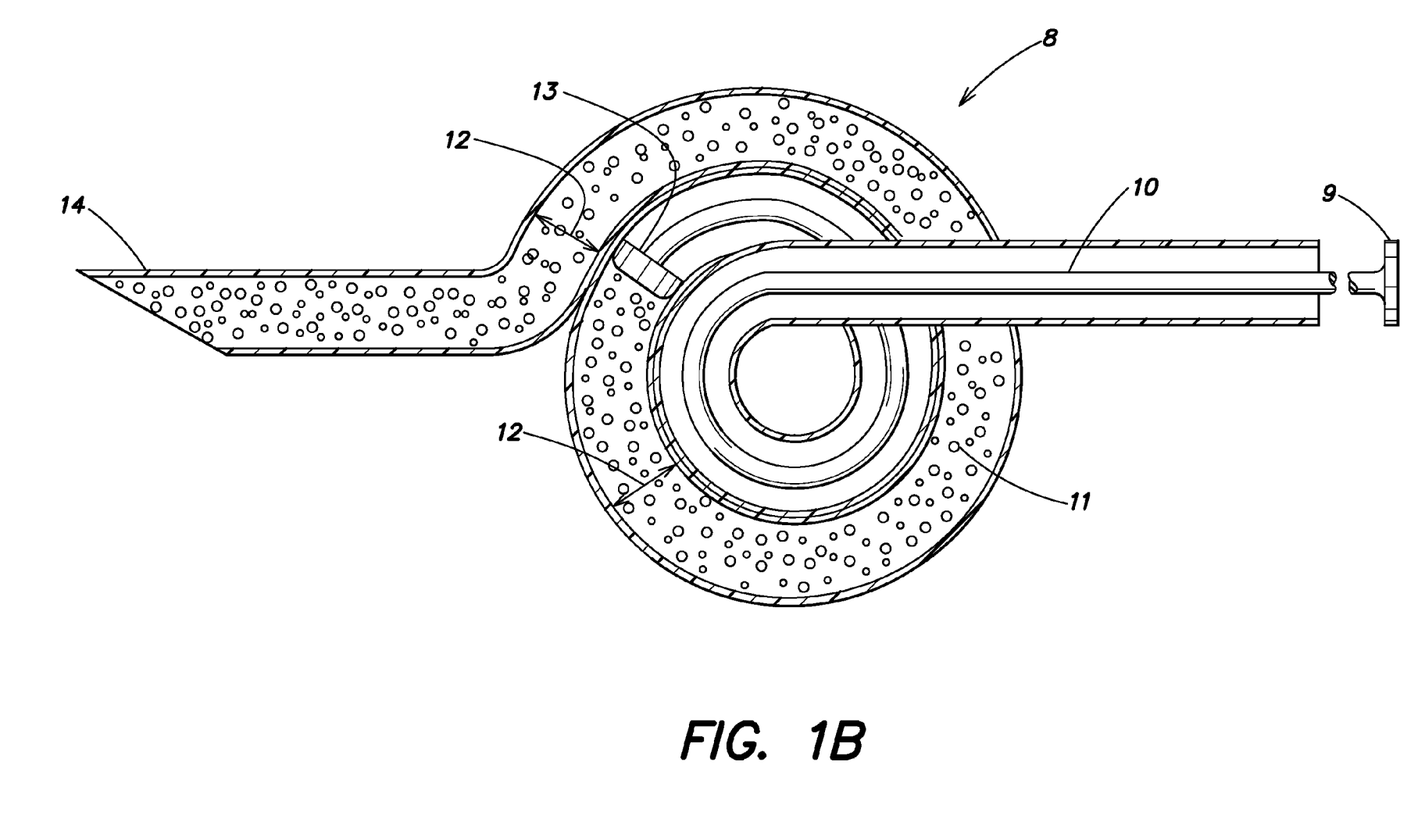
FIG. 1B is a representation of the same syringe with a beveled tip or dispensing end.

Other embodiments may be illustrated by reference to the syringe assembly of FIG. 1B. The assembly 8 has a syringe body with a constant lumen size 12. The plunger has a handle 9 and a connection part 10 that extends to the spacer 13. Force exerted by the spacer 13 on the contents 11 to be expelled, forces them toward and out of the barrel at end 14. The connector is shown as broken in order to denote a length that is longer than shown in the figure. As with other embodiments, a needle is optional.

Figures 2A, 2B:
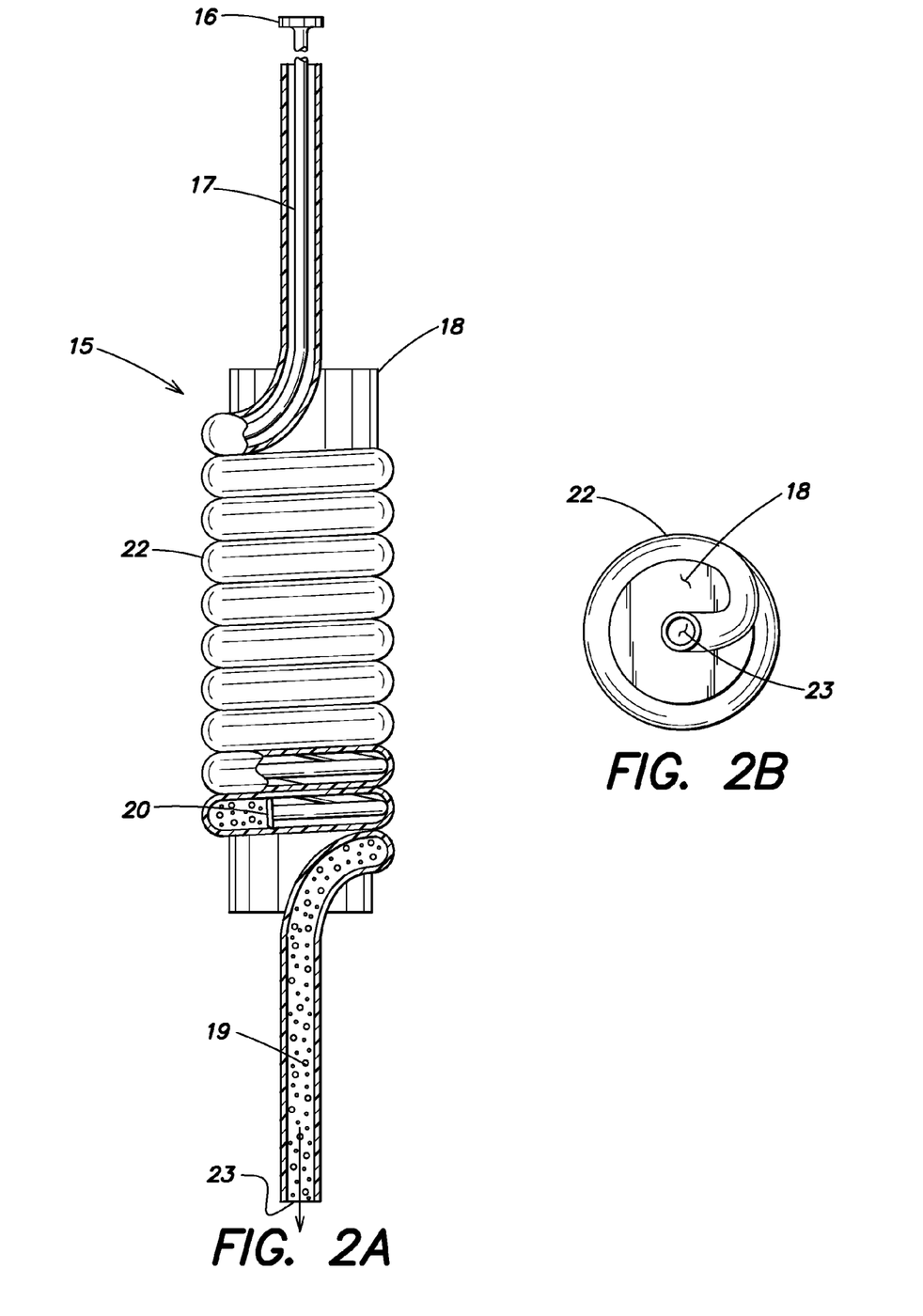
FIG. 2A is a representation of another embodiment of a bone graft injection syringe according to the present invention.
FIG. 2B is a bottom view of the syringe of FIG. 2A.

FIGS. 2A and 2B show another embodiment of the present invention. In FIG. 2A, the syringe assembly 15 is shown from the side. At one end there is a plunger 16 that is connected to the connector 17 and through which force can be applied and transferred to spacer 20. The plunger travels through the barrel 22 of the syringe. The barrel is shown wrapped around a cylinder 18, which may be a material such as plastic or metal. Part of the barrel is shown cut away so as to illustrate the location of the spacer and connector. The cylinder helps the syringe to retain its coil shape. Material 19 may be dispensed out of the end 23 of the syringe that is distal to the plunger handle.

FIG. 2B shows the syringe of FIG. 2A from a bottom view. For reference the barrel 22, the cylinder 18 and the end 23 through which material is dispensed are identified.

Figure 2C:
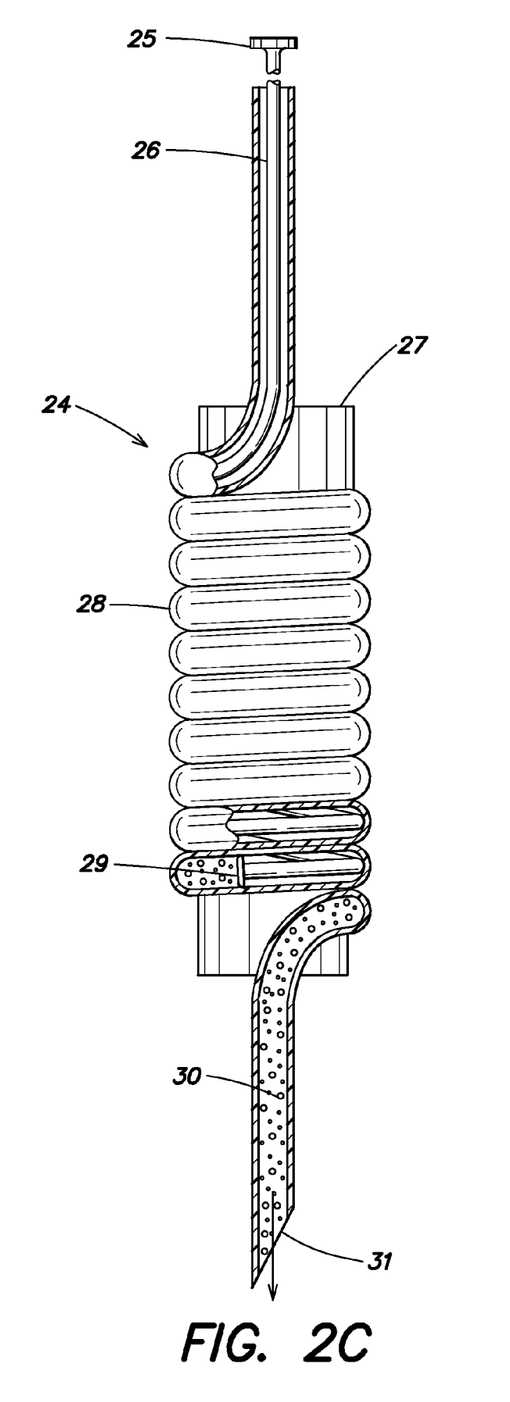
FIG. 2C is a representation of a syringe similar to that of FIG. 2A, but the tip is beveled.

FIG. 2C shows a syringe 24 that is similar to that of FIG. 2A, except, the end 31 through which material is dispense is beveled. Thus, shown are the handle 25, the connector 26 and the spacer 29 of the plunger, as well as the barrel of the syringe 28 and the bone graft material 30. Similarly, there is a cylinder 27 around which the coil is wrapped.

Figure 2D:
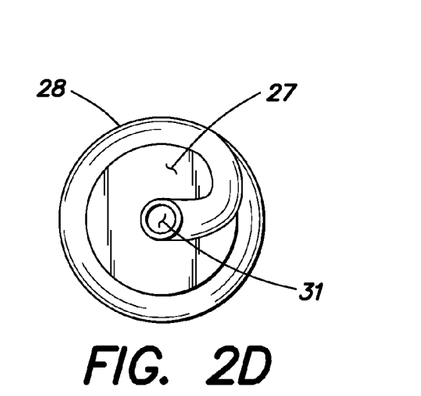
FIG. 2D is a representation of a bottom view of the syringe of FIG. 2C.

FIG. 2D is a bottom view of FIG. 2C. For reference the barrel 28, cylinder 27 and end for dispensing 31 are shown.

Figure 3A:
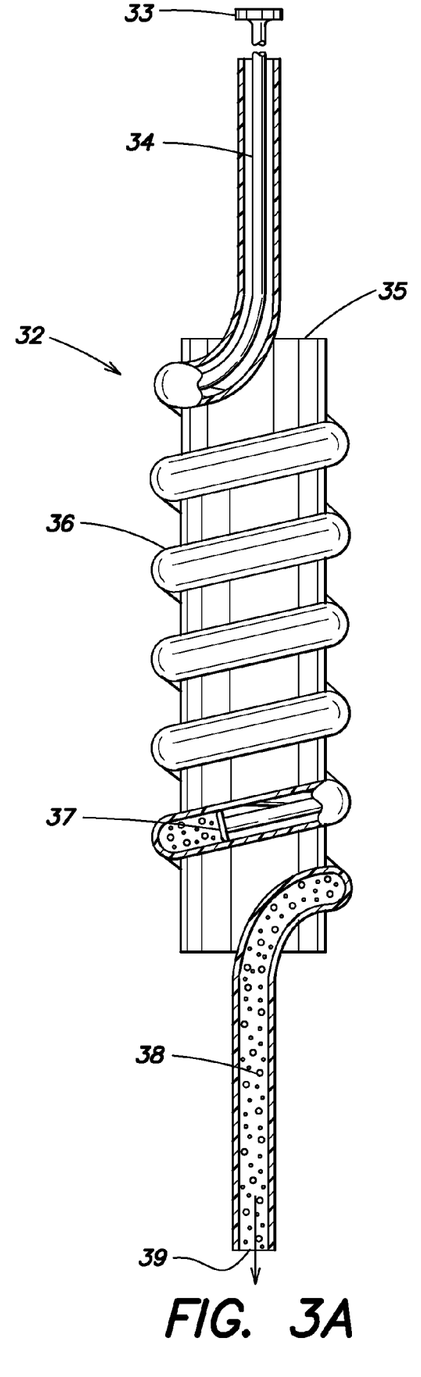
FIG. 3A is a representation of another embodiment of a bone graft injection syringe according to the present invention.

FIG. 3A shows another of a syringe assembly 32 of the present invention. The barrel 36 is shown less tightly wound than the barrel of FIGS. 2A and 2C. For reference, shown are the plunger handle 33, the connector 34, the spacer 37, the cylinder 35 around which the barrel is wound, the bone graft material 38 and blunt end 39 of the syringe, through which material is dispensed.

Figure 3B:
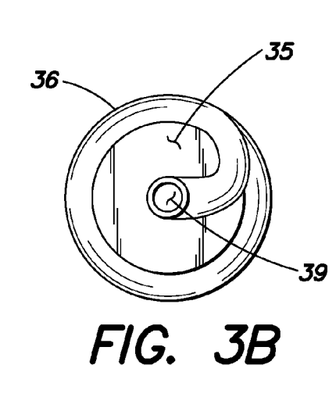
FIG. 3B is a bottom view of the syringe of FIG. 3A.

FIG. 3B shows the bottom view of the assembly of FIG. 3A. For reference, identified are the barrel 36, the cylinder 35 and the end 39 through which material is dispensed.

Figure 3C:
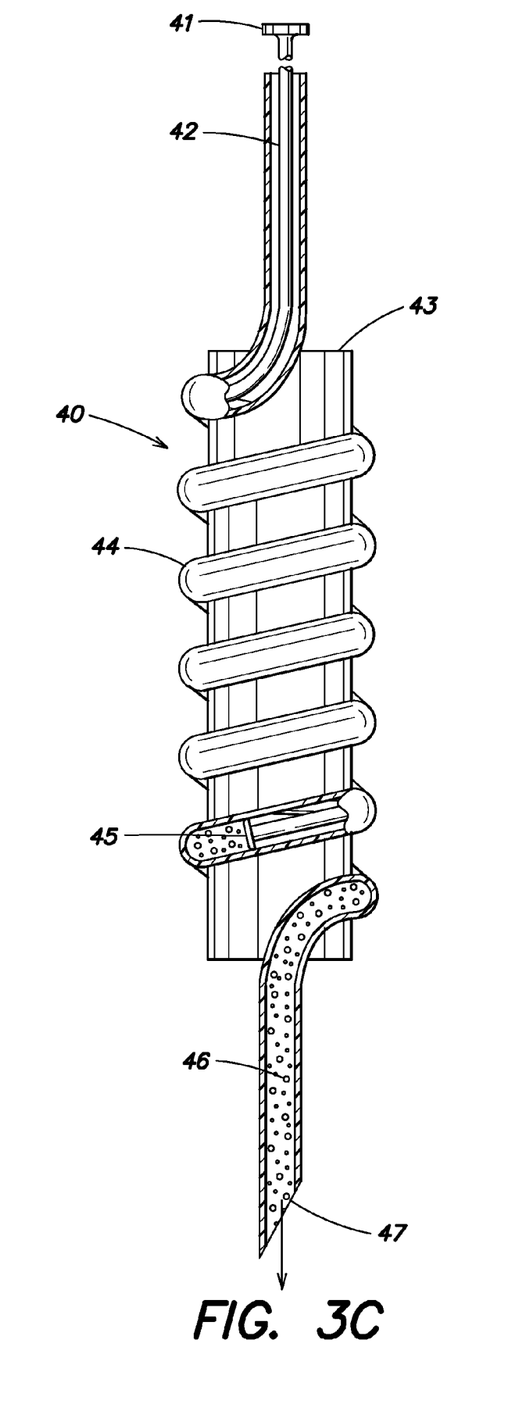
FIG. 3C is a representation of a syringe similar to that of FIG. 3A, but the tip is beveled.
Figure 3D:
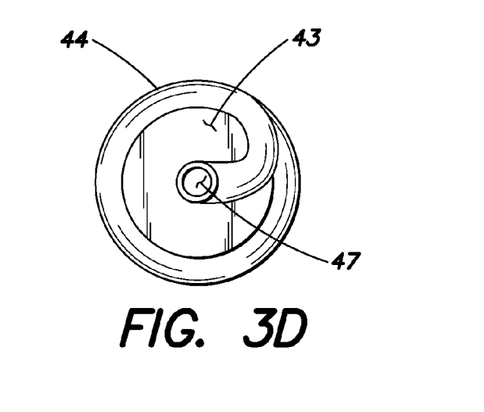
FIG. 3D is a representation of a bottom view of the syringe of FIG. 3C.

FIGS. 3C and 3D are similar to FIGS. 3A and 3B respectively. However, the end 47 through which material is dispensed is beveled. Thus, the assembly 40 shows a plunger handle 41 with a connector 42 that travels within barrel 44 to spacer 45, which pushes the bone graft material 46 out of opening 47.

Figure 4A:
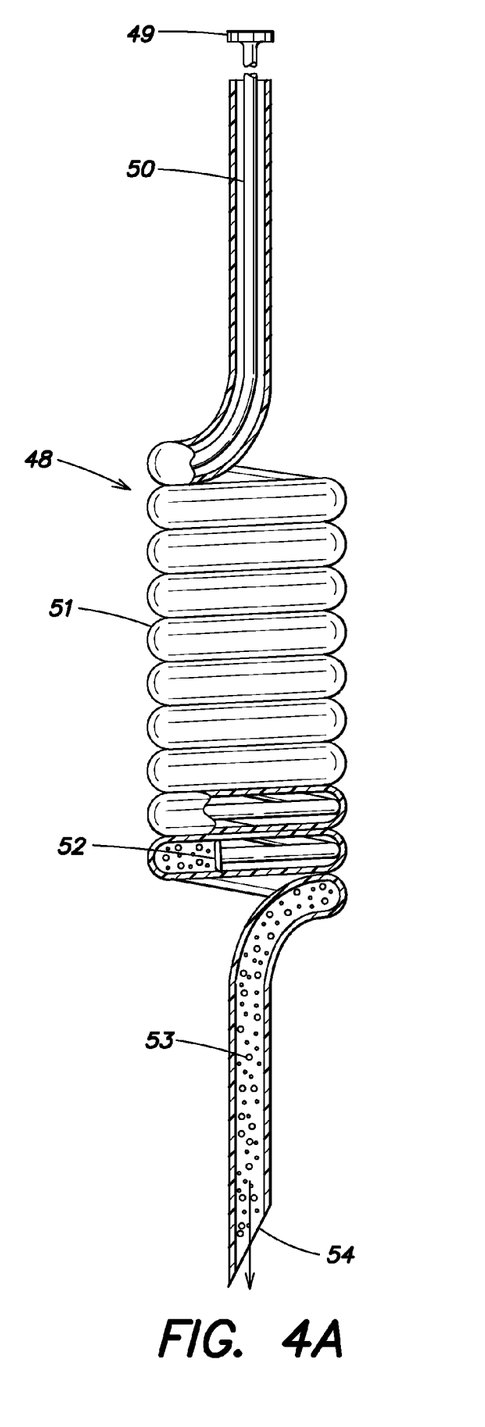
FIG. 4A is a representation of another embodiment of a bone graft injection syringe according to the present invention.

FIG. 4A shows another embodiment of the present invention. In this syringe assembly 48, the barrel 51 forms a coil shape, but is not wrapped around a cylinder. As with other embodiments, the plunger handle 49 is shown and force exerted on it may travel through the connector 50 to spacer 52. The force causes bone graft material 53 to exit through the beveled end 54 of the assembly.

Figure 4B:
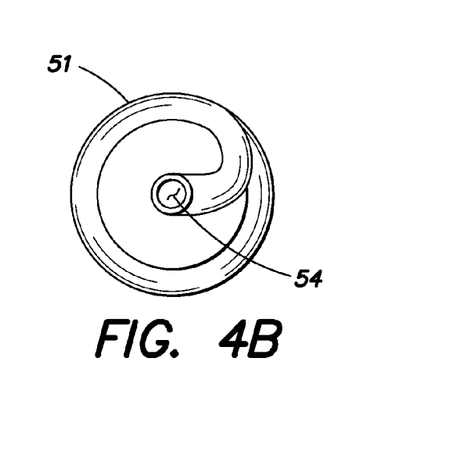
FIG. 4B is a bottom view of the syringe of FIG. 4A.

FIG. 4B shows a bottom view of the assembly of FIG. 4A. Identified are the barrel 51 and opening 54.

Figure 5A:
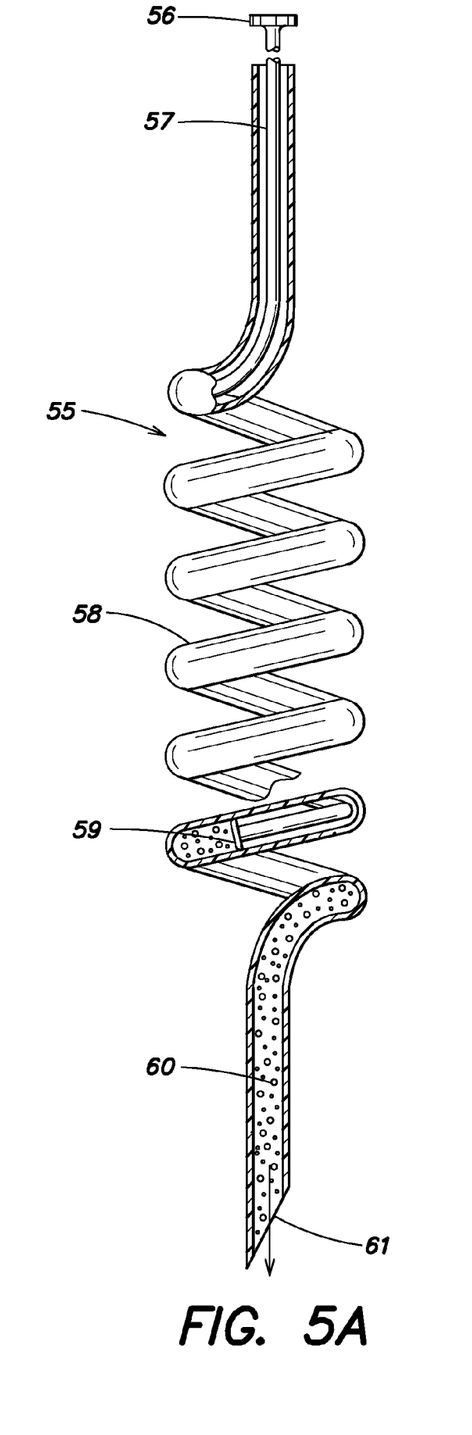
FIG. 5A is a representation of another embodiment of a bone graft injection syringe according to the present invention.

FIG. 5A shows a coil syringe assembly in which coils of the barrel 58 are spaced (i.e., the side of one coil does not touch the side of the next coil as in FIG. 4A). For reference, also shown is the plunger handle 56, the connector 57, the spacer 59, the bone graft material 60 and the opening of the syringe 61.

Figure 5B:
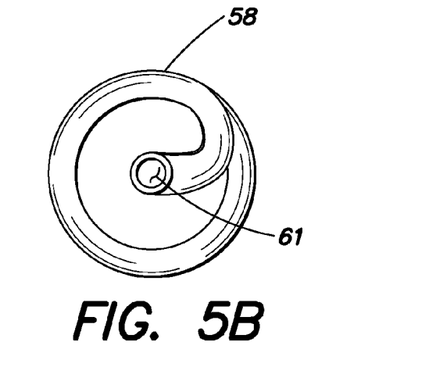
FIG. 5B is a bottom view of the syringe of FIG. 5A.

FIG. 5B shows a bottom view of the assembly of FIG. 5A. For reference, the barrel 58 and the end through which material is dispenses 61 are shown.

The syringe can be made from a variety of materials such as plastic, glass or metal or any combination thereof. For example, it may be made from a clear lipid resistant polycarbonate plastic.

Needles, which unless otherwise specified also refer to cannulas, may be tubes that are made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The needle may optionally include one or more tapered regions. In various embodiments, the needle may be beveled. The needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the needle may also be non-coring and have a sheath covering it to avoid unwanted needle sticks.

The preferable dimensions of the needle will, among other things, depend on the site for implantation. For example, the width of the epidural space is only about 3-5 mm for the thoracic region and about 5-7 mm for the lumbar region. Thus, the needle, in various embodiments, can be designed for these specific areas. Some examples of lengths of the needle may include, but are not limited to, from about 50 to 150 mm in length, for example, about 65 mm for epidural pediatric use, about 85 mm for a standard adult and about 110 mm for an obese adult patient. The thickness of the needle will also depend on the site of implantation. In various embodiments, the thickness includes, but is not limited to, from about 0.05 to about 1.655. The gauge of the needle may be the widest or smallest diameter or a diameter in between for insertion into a human or animal body. The widest diameter is typically about 14 gauge, while the smallest diameter is about 22 gauge. In various embodiments the gauge of the needle is about 18 to about 22 gauge.

Plungers

The plunger may be made from materials such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. In some embodiments, the plunger has a spacer, a connector and handle.

In various embodiments, the distance that the plunger advances is proportional to the force applied by the practitioner, and thus a practitioner can vary the rate at which he or she dispenses material, and the practitioner can also dispense less than the entire contents of the syringe by discontinuing the force on the plunger. In other embodiments, the plunger can be associated with a trigger mechanism. When activated, the trigger mechanism can cause the plunger to move further into the barrel and cause a predetermined volume of the contents of the barrel to be dispensed. In some embodiments, the activation of the trigger will cause the plunger to move forward a sufficient distance to dispense all of the contents of the barrel or about one-half of the contents, or about one-third of the contents, or about one-quarter of the contents or about one-fifth of the contents or about one-sixth of the contents or about one-eighth of the contents or about one-tenth of the contents or about one-twelfth of the contents or about one-twentieth of the contents.

In some embodiments, upon activation of the trigger the plunger may cause the syringe to dispense from about 0.1 cc to about 50 cc of from about 0.1 cc to 1 cc or from about 1 cc to about 5 cc or from about 5 cc to about 10 cc or from about 10 cc to about 15 cc or from about 15 cc to about 20 cc or from about 20 cc to about 25 cc.

In some embodiments, in a given syringe assembly the plunger may be configured to have both a trigger mechanism that can allow for a fixed amount of volume to be dispensed and a standard configuration that allows the practitioner to dispense any amount of volume, wherein the amount is directly proportional to the force applied.

Bone Graft Material

Bone graft materials can include bone particles from fully mineralized bone, and demineralized bone particles and combinations thereof. The bone particles can be autograft, allograft, xenogenic, transgenic bone particles or a combination thereof.

In some embodiments, the bone graft material includes bone cements. Bone cements are commonly provided in two or more components. The first component is usually a powder and the second component is usually in liquid form. Examples of bone cement materials include those based on acrylate materials that can react by polymerization to form acrylate polymers.

In some embodiments, the bone cement comprises powder that includes, for example, calcium phosphate based powders and poly-methyl-methacrylate based powders. Any of various osteoconductive powders, such as ceramics, calcium sulfate or calcium phosphate compounds, hydroxyapatite, magnesium and Si based cements, deproteinized bone, corals, and certain polymers, can alternatively or additionally be used in the bone cement.

Typically, a bone cement can be formed by mixing a liquid acrylate monomer with a powder such as acrylate polymer using a mixing element, where the mixing can be accomplished by hand or machine. The resulting mixture has a paste or dough-like consistency. Typically, the components of the mixture react, involving polymerization of the acrylate monomer and copolymerization with the acrylate polymer particles. The viscosity of the cement composition increases during the reaction, resulting in a hard cement. The curing reaction of a bone cement material is generally exothermic.

Typically, the bone cement is prepared prior to injection by mixing bone-cement powder (e.g., poly-methyl-methacrylate (PMMA)), a liquid monomer (e.g., methyl-methacrylate monomer (MMA)), an x-ray contrast agent (e.g., barium sulfate), and an activator of the polymerization reaction (e.g., N,N-dimethyl-p-toluidine) to form a fluid mixture. Other additives including but not limited to stabilizers, drugs, fillers, dyes and fibers may also be included in the bone cement. Because the components react upon mixing, immediately leading to the polymerization, the components of bone cement should be kept separate from each other until the user is ready to form the desired bone cement. Once mixed, the user must work very quickly because the bone cement sets and hardens rapidly.

Other examples of bone cement compositions and/or their uses are discussed in U.S. Patent Publication No. 20080109003, U.S. Pat. Nos. 7,138,442; 7,160,932 7,014,633; 6,752,863; 6,020,396; 5,902,839; 4,910,259; 5,276,070; 5,795,922; 5,650,108; 6,984,063; 4,588,583; 4,902,728; 5,797,873; 6,160,033; and EP 0 701 824, the disclosures of which are herein incorporated by reference.

In some embodiments, other additives can be mixed with the bone cement and this includes bioactive substances. Thus, one or more bioactive substances can be combined with the bone cement by soaking or immersing the bone cement in a solution or dispersion of the desired bioactive substance(s). Bioactive substances include physiologically or pharmacologically active substances that act locally or systemically in the host. In certain applications, the bone cement can be used as a time-release drug delivery device for drugs or other bioactive substances that are to be delivered to the surgical site.

Bioactive substances that can be readily combined with the bone cement include, e.g., collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin or gentamicin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as collagenase, peptidases, oxidases, etc.; polymer cell scaffolds with parenchymal cells; angiogenic agents or polymeric carriers containing such agents; collagen lattices; antigenic agents; cytoskeletal agents; cartilage fragments; living cells such as chondrocytes, bone marrow cells, mesenchymal stem cells, natural extracts, genetically engineered living cells or otherwise modified living cells; DNA delivered by plasmid or viral vectors; tissue transplants; demineralized bone powder; autogenous tissues such as blood, serum, soft tissue, bone marrow, etc.; bioadhesives, bone morphogenic proteins (BMPs); growth and differentiation factors (GDFs); osteoinductive factor; statin; fibronectin (FN), osteonectin (ON); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; or nucleic acids. When employed, the total amount of bioactive substance can represent from about 0.1 to about 60 weight percent of the osteoimplant.

In some embodiments, the bioactive agent is mixed before, with or after the bone cement is added to the container. In some embodiments, the bioactive agent comprises the family of proteins known as the transforming growth factor-beta (TGFβ) superfamily of proteins, which includes the activins, inhibins, or bone morphogenetic proteins (BMPs). In some embodiments, the active agent includes at least one protein from the subclass of proteins known generally as BMPs. BMPs have been shown to possess a wide range of growth and differentiation activities, including induction of the growth and differentiation of bone, connective, kidney, heart, and neuronal tissues. See, for example, descriptions of BMPs in the following publications: BMP-2, BMP-3, BMP-4, BMP-5, BMP-6, and BMP-7 (disclosed, for example, in U.S. Pat. Nos. 5,013,649 (BMP-2 and BMP-4); 5,116,738 (BMP-3); 5,106,748 (BMP-5); 5,187,076 (BMP-6); and 5,141,905 (BMP-7)); BMP-8 (disclosed in PCT WO 91/18098); BMP-9 (disclosed in PCT WO 93/00432); BMP-10 (disclosed in PCT WO 94/26893); BMP-11 (disclosed in PCT WO 94/26892); BMP-12 or BMP-13 (disclosed in PCT WO 95/16035); BMP-15 (disclosed in U.S. Pat. No. 5,635,372); BMP-16 (disclosed in U.S. Pat. No. 6,331,612); MP52/GDF-5 (disclosed in PCT WO 93/16099); or BMP-17 or BMP-18 (disclosed in U.S. Pat. No. 6,027,917). The entire disclosure of these references is herein incorporated by reference. Other TGF-proteins that may be useful as the active agent of the bone cement paste include Vgr-2 and any of the growth and differentiation factors (GDFs), such as, for example, GDF-5.

A subset of BMPs that may be used in certain embodiments includes BMP-2, BMP-4, BMP-5, BMP-6, BMP-7, BMP-8, BMP-9, BMP-10, BMP-11, BMP-12 or BMP-13. In some embodiments, the composition contains two or more active agents (e.g., BMP-2 and BMP-4). Other BMPs and TGF-proteins may also be used.

The active agent may be recombinantly produced, or purified from another source. The active agent, if a TGF-β protein such as a BMP, or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β (e.g., a heterodimer composed of one monomer each of a BMP and a related member of the TGF-β superfamily). Examples of such heterodimeric proteins are described, for example in published PCT Patent Application WO 93/09229.

In some embodiments, the amount of growth factor, (e.g., bone morphogenic protein) may be sufficient to cause bone growth. In some embodiments, the growth factor is rhBMP-2 and is contained in the bone graft material in an amount of from 1 to 2 mg per cubic centimeter of the bone graft material. In some embodiments, the amount of rhBMP-2 morphogenic protein is from 2.0 to 2.5 mg per cubic centimeter (cc) of the bone graft material.

In some embodiments, the growth factor is supplied in a liquid carrier (e.g., an aqueous buffered solution). Examples of aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the BMP-2 is provided in a vehicle (including a buffer) containing sucrose, glycine, L-glutamic acid, sodium chloride, and/or polysorbate 80.

The bone graft material may be mixed with additional therapeutic agents. Examples of therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

Examples of therapeutic agents suitable for use also include, but are not limited to, an anti-inflammatory agent or an analgesic agent. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In some embodiments, a statin may be used. Statins include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+) R and (−)-S enantiomers of the statin. In various embodiments, the statin may comprise a 1:1 racemic mixture of the statin.

One method of making the bone graft material includes adding the powder to the container and adding the liquid and other components to the container and mixing them with a mixing element. The mixing element can be placed in or attached to the upper opening of the container and the mixing element stirred by hand or machine until the desired consistency of the slurry or paste or liquid is reached. Optionally, the mixture can include one or more other optional components such as any of binders, fillers, plasticizers, biostatic/biocidal agents, surface active agents, bioactive substances, or reinforcing components. The syringe is then filled with the bone graft material and then delivered to the anatomic site as discussed above.

The bone graft material can be injected at the desired anatomic site, for example, a hard tissue repair site, e.g., one resulting from injury, defect brought about during the course of surgery, infection, malignancy or developmental malformation, or the like. The bone graft material can be utilized in a wide variety of orthopedic, periodontal, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repairs of spinal injuries, scoliosis, lordosis and kyphosis treatments, intermaxillary fixation of fractures, mentoplasty, temporomandibular joint replacement, alveolar ridge augmentation and reconstruction, onlay bone grafts, implant placement and revision, sinus lifts, etc. Specific bones that can be repaired or replaced with the osteoimplant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal or metatarsal bones.

In some embodiments, the bone cement comprises two separate components, one component being liquid and a second component being solid and the bone cement is mixed with the top opening while being exposed to room air.

Methods of Use

According to another embodiment, the present invention provides a method for injecting both graft materials. The method comprises loading a syringe of any of the embodiments of the present invention with a bone graft material; and pushing the plunger toward a first opening, thereby forcing the materials to exit the syringe. The syringe may be used to deliver bone graft material to anatomical structures during surgical procedures in order to aid in the bone regeneration process.

In operation, when a practitioner applies force to the exposed end of the plunger to express the plunger, the distal end of the plunger, which is the end that contacts the bone graft material, and may have a plunger seal or spacer, forces the bone graft material through the inner chamber of the barrel and out of the first end of the barrel. At the first end there may optionally be an adapter that permits the material to move through it to the hollow portion of a needle, and as desired to a surgical site. The aforementioned spacer (also referred to as the plunger seal) is designed to expel all of the contents in the inner chamber without allowing any of those contents to pass behind it. The spacer may, for example, be made of rubber, silicone, or plastic or combinations thereof.

In order to further facilitate movement of bone graft material through the barrel, blood or other fluid may be introduced to the bone graft material within the barrel. For example, a liquid, gel or fluid may be added to the chamber of the barrel either before or after the addition of the bone graft material. The fluid may, for example, be introduced by a needle or other device through an adapter at the first end of the barrel. The adapter permits materials to enter or exit upon the creation of a vacuum or addition of force, respectively. Alternatively, the liquid, gel or fluid, and/or bone graft materials may be introduced through a side port in the barrel or at the second end of the barrel if an orifice is present there.

The various fluids that may be added to the inner chamber include sterile water, saline, blood, or blood components including plasma, platelet-rich plasma, buffy coat, autologous growth factors or other concentrated blood components, red blood cells, white blood cells or platelets in any combination, as well as cryoprecipitates. Other suitable and intended fluids include bone marrow, as well as growth factor solutions suspensions or gels, which include any of the well known growth factors, such as Platelet-Derived Growth Factor (PDGF), Transforming Growth Factor Beta (TGF-β), Insulin-Like Growth Factor (IGF), Fibroblast Growth Factor (FGF), Epidermal Growth Factor (EGF), Vascular Endothelial Growth Factor (VEGF), Bone Morphogenetic Proteins (BMPs), and vectors for gene therapy. Further, cellular solutions, suspensions, and materials including osteoblasts, osteoprogenitor cells, chondroblasts, stem cells, or fibroblasts may also be used, as well as solutions or suspensions containing other therapeutic agents such as antibiotics, analgesics, antithrombinolytics, or chemotherapeutic agents. Further, bone graft replacements, such as recombinant bone morphogenetic proteins, may be added.

In some embodiments, the bone graft materials may for example, comprise one or more of ceramic particles, and bone particles, each of which can improve efficacy of bone grafting products and provide compression resistance. The bone graft materials may also, or alternatively, comprise collagen (including cross-linked collagen) demineralized bone matrix particles, growth factors, antibiotics, analgesics, and combinations thereof.

In some embodiments, the bone graft replacement material comprises a putty, a bone cement or combinations thereof. Bone cements are commonly provided in two or more components. The first component is usually a powder and the second component is usually in liquid form. Examples of bone cement materials include but are not limited to those based on acrylate materials that can react by polymerization to form acrylate polymers. Typically, a bone cement can be formed by mixing a liquid acrylate monomer with a powder such as acrylate polymer using a mixing element, where the mixing can be accomplished by hand or machine. The resulting mixture has a paste or dough-like consistency. Typically, the components of the mixture react, involving polymerization of the acrylate monomer and copolymerization with the acrylate polymer particles. The viscosity of the cement composition increases during the reaction, resulting in a hard cement. The curing reaction of a bone cement material is generally exothermic.

Kits

The invention also provides a kit for use in mixing a fluid with a porous or non-porous solid bone graft materials. The kit comprises a syringe assembly as discussed in the foregoing paragraphs, and may also include a container having a solid or porous particulate or granular bone graft material, such as an optional vial or container of a bone promoting agent. The solid material may be hydroxyapatite granules, for example. The bone repair promoting agent may be in solid or liquid form, and may include (for example) blood or a component thereof, or natural or recombinant bone growth factors, or other agents useful for stimulating bone repair or growth.

In some embodiments, such solids can include, for example, autogenous morselized bone graft, autogenous bone graft strips, allograft chips, demineralized bone matrix in putty, gel, strip, or other forms, xenografts and fired bone. The solids can also be bone graft substitutes, such as hydroxyapatite, calcium carbonate, beta tricalcium phosphate, calcium sulfate or mineralized collagen. In addition, bone graft materials may comprise natural or synthetic polymers such as collagen particles, meshes, sponges, and gels, hyaluronic acid and derivatives thereof, liposomes or other natural biomaterials known as potential implants, or carriers of therapeutic agents, such as cytokines, growth factors, cells, antibiotics, analgesics, chemotherapeutic drugs, and the like.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A syringe assembly for dispensing bone graft material comprising:
    a barrel having a first opening and second opening, the barrel defining a cavity and including first and second sections each with a curvature over at least ninety degrees, the first and second sections being oriented such that an upper surface of the first section engages a lower surface of the second section, wherein the curvature forms a cylindrical coil shape, and having an internal radius of about 0.3 cm to about 1 cm and a length of from about 5 cm to about 50 cm;
    a cylinder, the barrel being wrapped around the cylinder to retain the cylindrical coil shape;
    a flexible plunger, wherein said flexible plunger is sized to slide within the cavity; and
    a trigger mechanism associated with the plunger, wherein the trigger mechanism causes the plunger to slide a predetermined distance through the cavity so as to dispense a predetermined, fixed volume of bone graft material.

2. The syringe assembly of claim 1 further comprising a hollow needle.

3. The syringe assembly of claim 2, wherein the hollow needle is attached to the first opening.

4. The syringe assembly of claim 1, wherein the barrel defines a cavity of uniform diameter.

5. The syringe assembly of claim 1, wherein the barrel comprises clear lipid resistant polycarbonate plastic and the curvature has a uniform radius.

6. The syringe assembly of claim 1, wherein the curvature moves through two dimensions.

7. The syringe assembly of claim 1, wherein the curvature moves through three dimensions.

8. The syringe assembly of claim 1, wherein the curvature has an increasing radius as the cavity moves toward the first opening.

9. The syringe assembly of claim 1, wherein the curvature has a decreasing radius as the cavity moves toward the first opening.

10. The syringe assembly of claim 1 further comprising an opening in a side of the barrel.

11. A method for injecting bone graft materials comprising:
    loading the syringe of claim 1 with a bone graft material; and
    pushing said plunger toward said first opening, thereby forcing said bone graft materials to exit said syringe.

12. The method according to claim 11, wherein the bone graft material comprises ceramic particles.

13. The method according to claim 11, wherein the bone graft material comprises at least one of bone particles and demineralized bone particles.

14. The method according to claim 11, wherein the bone graft material comprises at least one of BMP-2, BMP-6, BMP-7, GDF-5, a statin or demineralized bone.

15. The method according to claim 14, wherein the bone graft material further comprises an analgesic, an antibiotic or a combination thereof.

16. A kit for delivering bone graft material comprising: the syringe assembly of claim 1; and
    a bone graft material.

17. The kit of claim 16, wherein the syringe assembly is pre-loaded with the bone graft material.

18. The kit of claim 16, wherein the barrel has a curvature of from about ninety degrees to about three hundred and sixty degrees.

19. The kit of claim 18, wherein the curvature is from about ninety to about one hundred and eighty degrees.

* * * * *